United States Patent [19]

Parsons et al.

[11] Patent Number: 5,056,521
[45] Date of Patent: Oct. 15, 1991

[54] METHOD FOR MONITORING GLUCOSE LEVEL

[75] Inventors: J. Stuart Parsons, Laguna Niguel; Jon Booher, Lake Forest, both of Calif.

[73] Assignee: Health Craft International, Inc., Pasadena, Calif.

[21] Appl. No.: 374,535

[22] Filed: Jun. 29, 1989

[51] Int. Cl.$^5$ ............................................. A61B 10/00
[52] U.S. Cl. .................................. 128/635; 128/760; 128/898; 204/403; 324/713; 324/724
[58] Field of Search ............... 128/635, 741, 760, 787, 128/898; 204/153.12, 403; 324/692, 713, 724

[56] References Cited

U.S. PATENT DOCUMENTS

| | | | |
|---|---|---|---|
| 4,123,701 | 10/1978 | Josefsen et al. | 324/692 |
| 4,273,639 | 6/1981 | Gottermeir | 204/416 |
| 4,750,496 | 6/1988 | Reinhart et al. | 128/635 |
| 4,759,828 | 7/1988 | Young et al. | 204/153.12 |
| 4,872,956 | 10/1989 | Kotani et al. | 204/403 |
| 4,891,104 | 1/1990 | Liston et al. | 204/153.12 |

FOREIGN PATENT DOCUMENTS

| | | | |
|---|---|---|---|
| 3293439 | 11/1988 | Japan | 128/760 |
| 3293440 | 11/1988 | Japan | 128/760 |

*Primary Examiner*—Lee S. Cohen
*Assistant Examiner*—K. M. Pfaffle
*Attorney, Agent, or Firm*—Christie, Parker & Hale

[57] ABSTRACT

A sample of oral fluid is collected by an absorbent non-reactive collecting swab brought into contact with a favorable surface in the oral cavity. The fluid is interstitial transudate selectively collected from the vestibule region of the oral cavity at the junction of the superior labial mucous membrane and the superior gingivae between the upper canine teeth. The collecting swab is an open cell foam material with a fine (e.g., 0.3 mm diameter) cell size. The collecting swab is placed in a cylindrical concentrator and the fluid sample is squeezed through a small hole in the concentrator by pushing a plunger into the concentrator and squeezing the fluid from the collecting swab into a monitoring instrument located off site. A common electronic circuit in the instrument generates an electrical glucose representative readout for oral fluid or whole blood. A sheet of graph paper has rectangular coordinates one of which represents glucose level and the other which represents time of day. The first coordinate of the graph paper is mounted on a flat surface adjacent to a linear glucose level display. The user can record readings on the linear display by simply projecting such readings laterally on the graph to the applicable time of day and placing a mark on the graph. In the instrument, an enzyme electrode receives the sample from the concentrator. The electrode has a membrane that is wetted by a buffer solution when not in use.

5 Claims, 8 Drawing Sheets

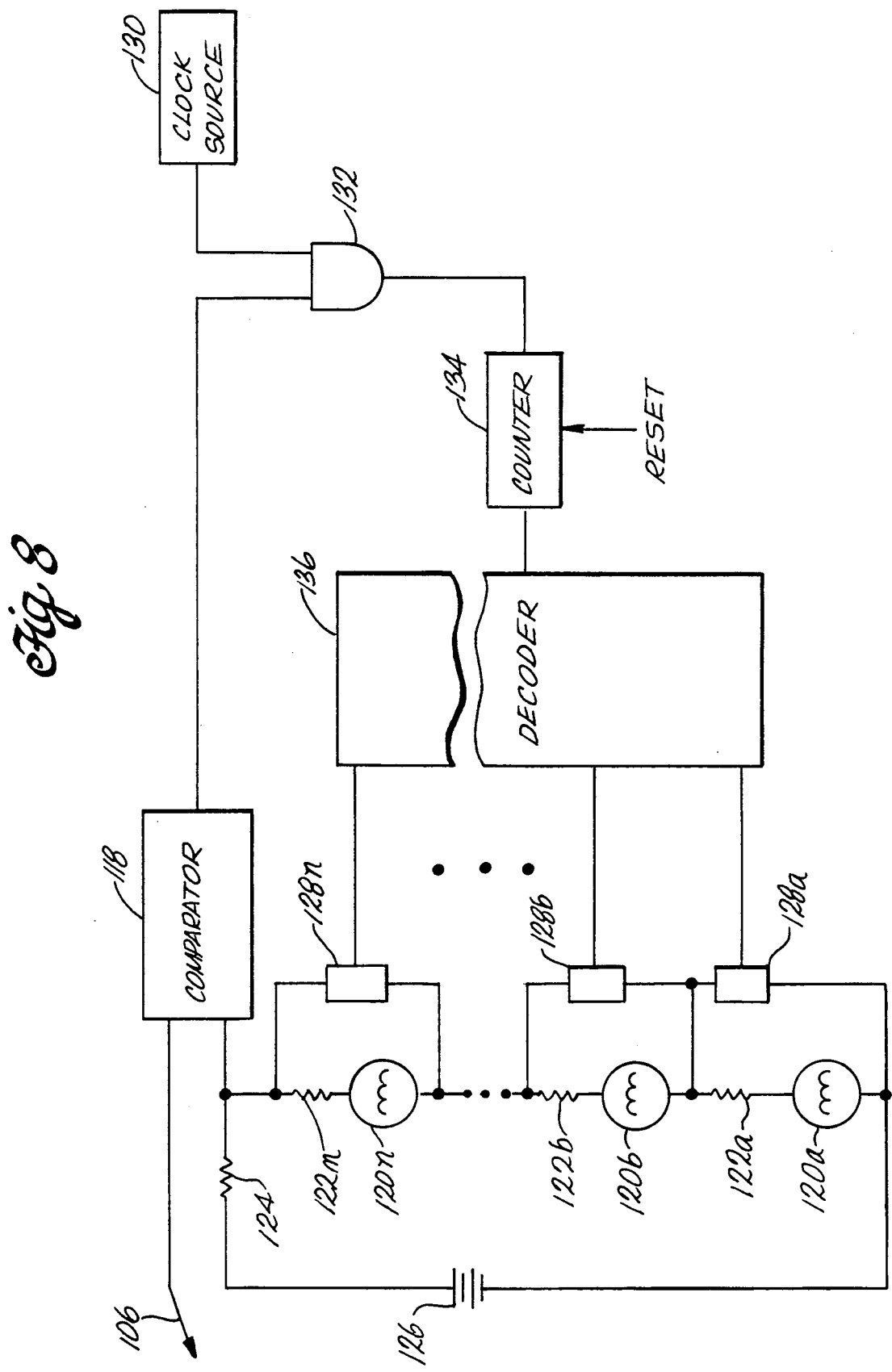

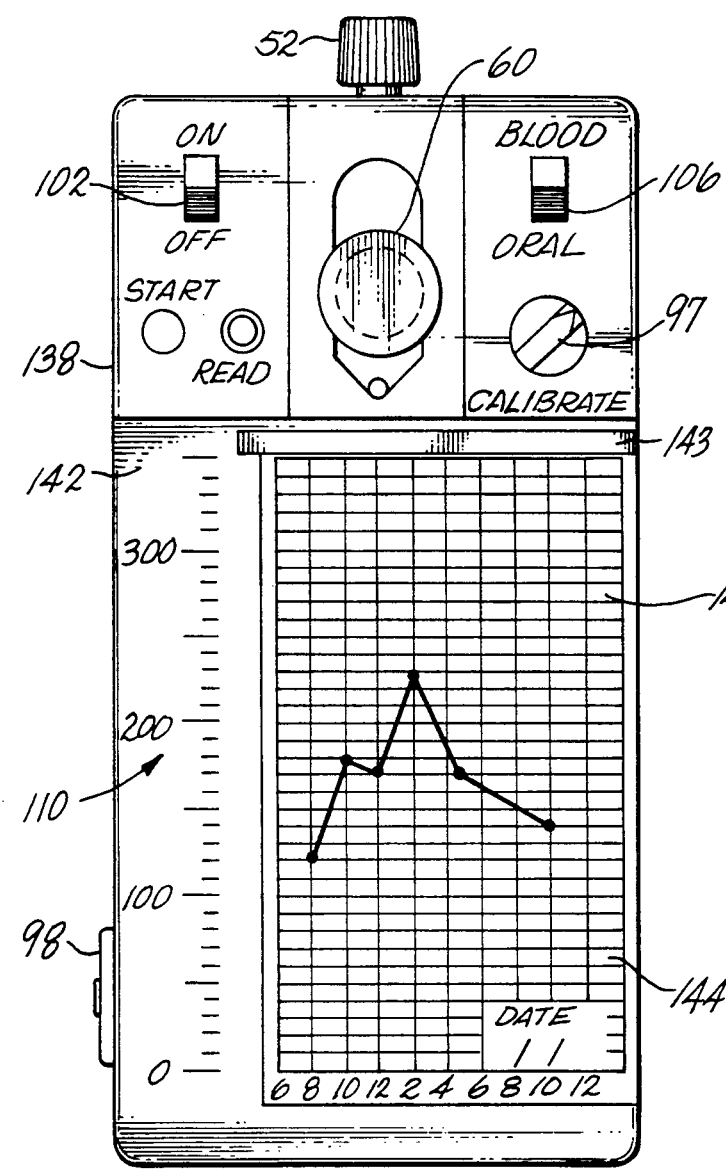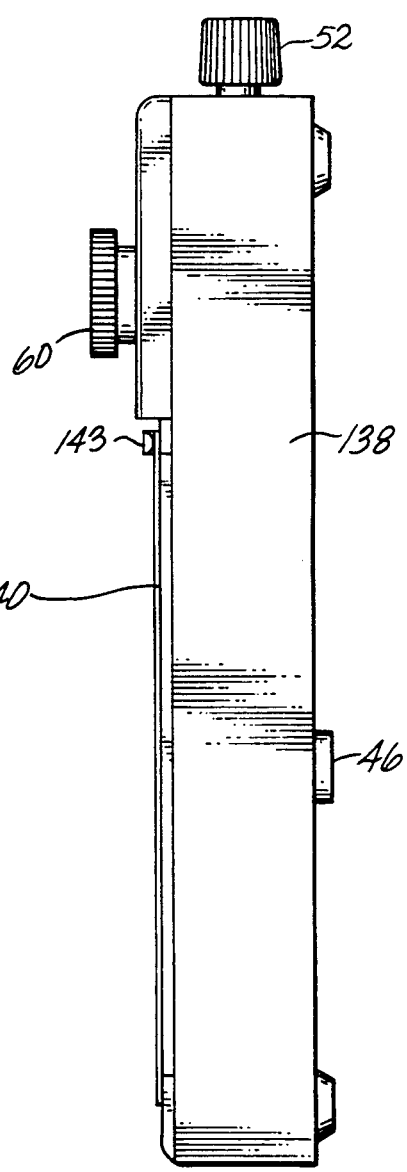

METHOD FOR MONITORING GLUCOSE LEVEL

BACKGROUND OF THE INVENTION

This invention relates to the field of medical testing and, more particularly, to a method and apparatus for measuring human glucose levels.

For a number of years, polarographic systems with an enzyme electrode have been used to measure glucose level in blood samples. For example, Clark Patent 3,539,455 teaches the use of a platinum anode and silver cathode to measure the hydrogen peroxide produced by the reaction of glucose and oxygen in the presence of a glucose oxidase enzyme. Newman Patent 3,979,274 discloses a laminated membrane for an enzyme electrode in which the enzyme is coupled with an adhesive between the lamina. The lamina of the multi-ply membrane comprise an outer support layer that serves as a barrier to high molecular weight substances and an inner homogeneous layer that serves as a barrier to interfering low molecular weight materials, but permits hydrogen peroxide to pass through, and an intermediate enzyme layer that reacts with glucose and bonds the outer and inner layers together. Glucose passes through the outer layer and reacts with a surplus of oxygen in the presence of the contained enzyme. Hydrogen peroxide, which is one of the reaction products, passes through the inner layer to the electrode. The resulting electric current is a measure of the level of glucose in the sample fluid under test.

Reinhart Patent 4,750,496 teaches the use of the described polarographic cell system to measure the glucose level (concentration) on a mucosal surface in the oral cavity of a living being. Specifically, the enzyme electrode membrane of a glucose monitoring instrument is positioned on the buccal mucosa, and a surplus of oxygen from the atmosphere is conveyed to the membrane through a passageway in the instrument. The oxygen reacts with the glucose that migrates through the outer layer of the membrane in the present of the enzyme, and the resulting hydrogen peroxide migrates through the inner layer of the membrane to the electrodes while the membrane remains in contact with the mucosal surface. Thus, a noninvasive glucose measurement is made on a sample of mucosal fluid of patient in situ, rather than carrying a blood fluid sample to a free standing instrument.

SUMMARY OF THE INVENTION

According to one aspect of the invention, a sample of oral fluid is collected by an absorbent, nonreactive collecting swab brought into contact with a specifically favorable surface in the oral cavity. The collecting swab is carried to a free-standing glucose monitoring instrument located off site where a measurement of the glucose level is made by a polarographic cell with an enzyme electrode. This simplifies the glucose monitoring procedure and eliminates membrane contact as a variable in the test procedure.

According to another feature of the invention, a specific oral fluid, namely interstitial transudate, is selectively collected from the vestibular region of the oral cavity at the junction of the superior labial mucous membrane and the superior gingivae medial to the two upper canine teeth. A sample taken from this region of the oral cavity is relatively free of other body fluids, particularly saliva because of the anatomical remoteness of the salivary glands, and is believed to be better representative of the interstitial glucose concentration of the patient and/or the insulin requirements of diabetics. Preferably the glucose sample is carried to a free-standing glucose monitoring instrument located off site.

According to another feature of the invention, the nonreactive fluid collecting swab is an open cell foam or sponge material with a fine (e.g., 0.3 mm diameter) cell size. To introduce the fluid sample into the monitoring instrument, the collecting swab is placed in a cylindrical concentrator and the fluid sample is squeezed through a small hole in the concentrator by pushing a plunger into the concentrator and squeezing the fluid from the collecting swab. By virtue of the small cell size of the collecting swab, the viscous glycoprotein of the sample is retained by the collecting swab as the aqueous low viscosity glucose solution is expelled. As a result, few air bubbles are formed in the fluid sample delivered to the membrane and good fluid-membrane contact is achieved in the monitoring instrument.

According to another feature of the invention, a handheld, self-operable glucose monitoring instrument has an interior chamber defined in part by the outer surface of a filter membrane of an enzyme electrode. When the instrument is not in use, a buffer fluid covers and wets the membrane. In preparation for use of the instrument the buffer fluid is withdrawn from the membrane, and the membrane is exposed to a fixed volume sample of oral fluid or alternatively whole blood. Preferably the instrument has a capped filler and venting port, a capped sample access port, and a piston to withdraw the buffer fluid from and return it to the membrane.

According to another feature of the invention, a common electronic circuit generates an electrical readout, representative of glucose concentration in the oral fluid or whole blood. The circuitry comprises a voltage divide: driven by an operational amplifier.

Another feature of the invention is a glucose level logging system, preferably incorporated into the abovedescribed instrument. A sheet of graph paper has rectangular coordinates, one of which represents glucose level and the other of which represents time of day. The first coordinate of the graph paper is mounted on a flat surface adjacent to a linear glucose level display. The user can record readings on the linear display by simply projecting such readings laterally on the graph to the applicable time of day and placing a mark on the graph.

BRIEF DESCRIPTION OF THE DRAWINGS

The features of specific embodiments of the best mode contemplated of carrying out the invention are illustrated in the drawings, in which:

FIG. 8 is a schematic circuit diagram of the display driver of FIG. 7 for linear display;

FIG. 9 is a front view of the outer casing of the instrument of FIG. 3; and

FIG. 10 is a side elevation view of the outer casing of the instrument of FIG. 3.

DETAILED DESCRIPTION OF THE SPECIFIC EMBODIMENTS

Figure 1:
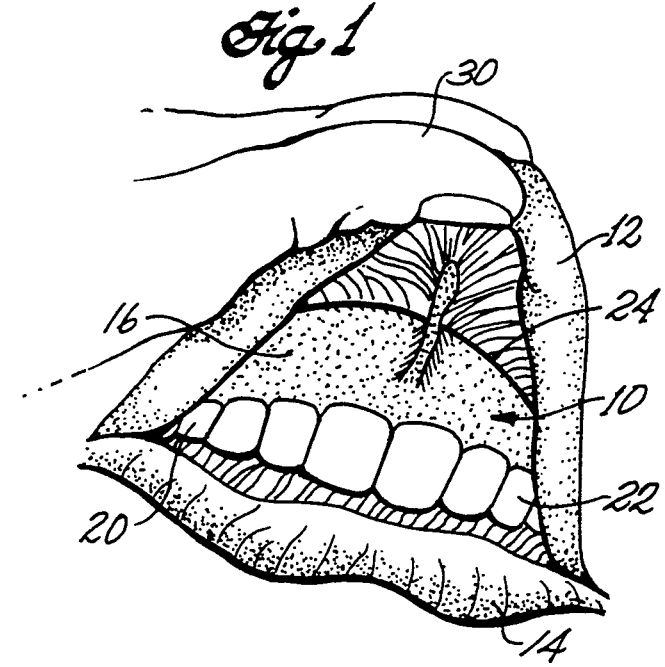
FIG. 1 is a diagram of a human mouth showing the preferred noninvasive sample collection site for practicing the invention.
Figure 2:
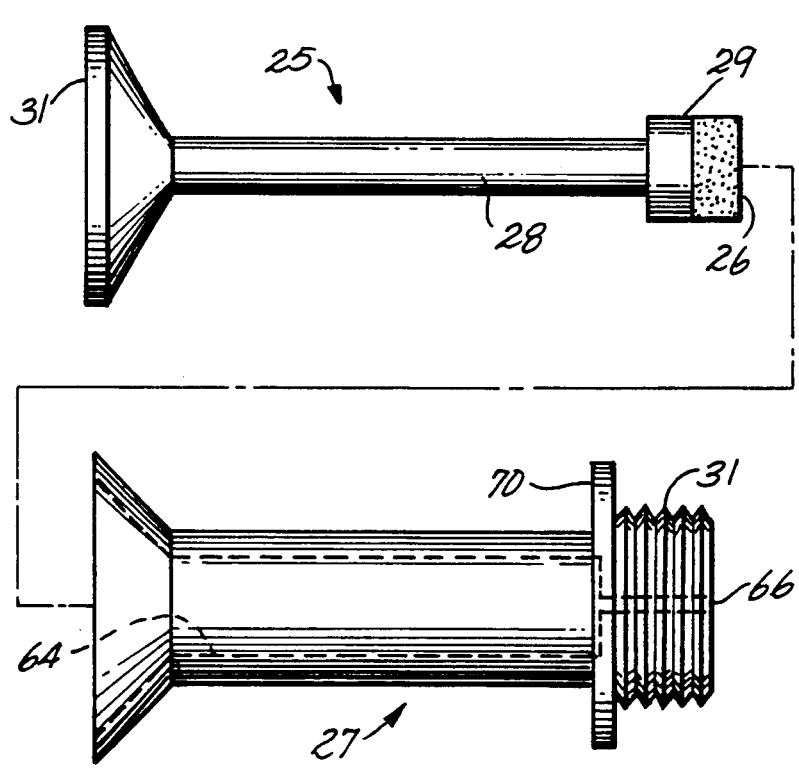
FIG. 2 is a side elevation view of the preferred sample collection and delivery system.

In FIGS. 1 and 2 an oral cavity 10 of a human patient is partially defined by an upper lip 12 and a lower lip 14. Within oral cavity 10, the upper jaw has a gum structure 16 that supports a set of teeth 18, including canine teeth 20 and 22. According to one aspect of the invention, the preferred site selectively to collect a sample of oral fluid for glucose level measurement, specifically interstitial transudate, is the region at the junction of upper gum structure 16 and upper lip 12 between the upper canine teeth 20 and 22 as represented by a dark line 24. In anatomical terms, the preferred region for sample collection is the vestibule of the oral cavity at the junction of the superior labial mucous membrane and the superior gingivae between the upper canine teeth. Interstitial transudate is believed to be the best indicator of glucose level and/or insulin requirements of diabetics because it originates in the intercellular space, it has a chemical composition similar to whole blood, and it has a consistent flow rate independent of nervous stimuli. This region is remote from other sources of body fluid that have variable flow rates, such as the salivary glands, and is therefore devoid of uncontrolled oral fluids that might distort the glucose level in the sample by diluting the desired fluid, namely interstitial transudate.

Although it is within the scope of the invention to measure glucose level in situ at region 24, it is preferable to collect a sample of oral fluid with a nonreactive absorbent collecting swab. To this end, with reference to FIG. 2, a fluid collection and delivery system comprises a wand 25 and a concentrator 27. Wand 25 has a nonreactive absorbent collecting swab 26 secured to a rubber piston 29, for example, by a nonreactive adhesive. Piston 29 is formed on one end of an elongated probe 28 and a thumb pad 31 is formed on the other end of probe 28. Collecting swab 26 is preferably shaped to conform to the shape of the crease of region 24, i.e., the end of collecting swab 26 is preferably tapered to maximize the surface contact with region 24 and to minimize contact with adjacent surfaces of the oral cavity. Collecting swab 26 is preferably made from an open cell foam or sponge material of small cell size (e.g. about 0.3 mm). Concentrator 27 has a cylindrical bore 64 that opens directly to the exterior at one end and is connected to the exterior by a small diameter exit opening 66 at the other end. Typically, exit opening 66 has a diameter of about 10 mils. An externally threaded section 31 and a flange 33 are formed around exit opening 66.

To collect a sample, the patient pulls upper lip 12 outwardly away from gum structure 16 with the fingers of one hand, as represented at 30 in FIG. 1, and wipes collecting swab 26 back and forth across region 24 by holding probe 28 in the other hand(not shown), without touching adjacent surfaces of oral cavity 10, until collecting swab 24 is saturated with oral fluid. This normally takes from a few seconds up to half a minute depending on the patient and the size of the sample. The delivery of the sample by concentrator 27 is discussed in detail below in connection with the glucose monitoring instrument.

The interior of the glucose monitoring instrument is shown in FIGS. 3 to 6. The instrument has a nonconductive housing 34 that defines a multipart chamber. The chamber may be considered functionally as comprising a reservoir 36 in communication with a sample delivery section 38, a fluid supply and withdrawal cylinder 40, and an interconnecting passage 42. A piston 44 rides in cylinder 40. The end of piston 44 has a protrusion 46 that extends through a slot 48 in housing 34 to permit the patient to slide piston 44 back and forth in cylinder 40 from the exterior of housing 34. A threaded filler and venting port 50 opens into reservoir 36 from the exterior of the instrument. Port 50 is normally closed by a threaded cap 52. A pedestal 54 is formed inside housing 34 as an enclosure for a replaceable integral enzyme electrode 56. A fluid sample delivery port 58 opens into section 38 opposite the end of pedestal 54. Pedestal 54 serves to position the membrane of electrode 56 in closely spaced relationship to port 58. Port 58 has internal threads that engage the threads on an access cap 60. A buffer fluid which could be water or an aqueous solution totally devoid of glucose (or with a fixed known quantity thereof to perform calibration) completely fills the chamber in housing 34 when piston 44 is depressed. As a result, buffer fluid covers and wets the membrane of electrode 56. When wand 25 is inserted into concentrator 27, piston 29 is moveable in bore 64 with a snug fit. Flange 70 controls the depth of insertion of concentrator 62 into the instrument. Threaded section 72 matches the threads on port 58.

Electrode assembly 56 comprises an inner cylindrical platinum anode 74, an annular silver cathode 76 coaxial therewith, and an insulator 78 therebetween. Assembly 56 is an integral, replaceable unit. A replaceable three-ply membrane 80 having the characteristics described in U.S. Pat. No. 3,979,274 referenced above, is stretched across one side of and attached to an O-ring 82. Electrode 56 is disposed in a bore 84 of pedestal 54. A counterbore 86 leads from bore 84 to section 38. Membrane 80 lies against electrode 56 and O-ring 82 is compressed between a shoulder formed at the end of bore 84 and the end of electrode 56 by an electrical connector 81 screwed into a threaded connection with bore 84. Connector 81 has a central electrical contact 83 that bears against cathode 74 and a concentric annular electrical contact 85 that bears against anode 76. An insulator 87 lies between contacts 83 and 85. O-ring 82 prevents leakage of fluid between electrode 56 and bore 84. The space circumscribed by 0-ring 82 defines a well 88 that communicates with bore 64 of concentrator 62 via exit opening 66. A surplus of oxygen must be available to membrane 80 d:!ring the test so the hydrogen peroxide produced by the chemical reaction is directly related to the glucose level in the sample. To replace electrode 56 or membrane 80, connector 81 is unscrewed and electrode 56 and/or membrane 80 is removed.

To make a glucose measurement the following sequence of steps is followed:

1. Collecting swab 26 is saturated with a sample, either oral fluid obtained noninvasively, as described in FIGS. 1 and 2, or blood whole blood obtained invasively.

2. The zero setting of the instrument is adjusted.

Figure 3:
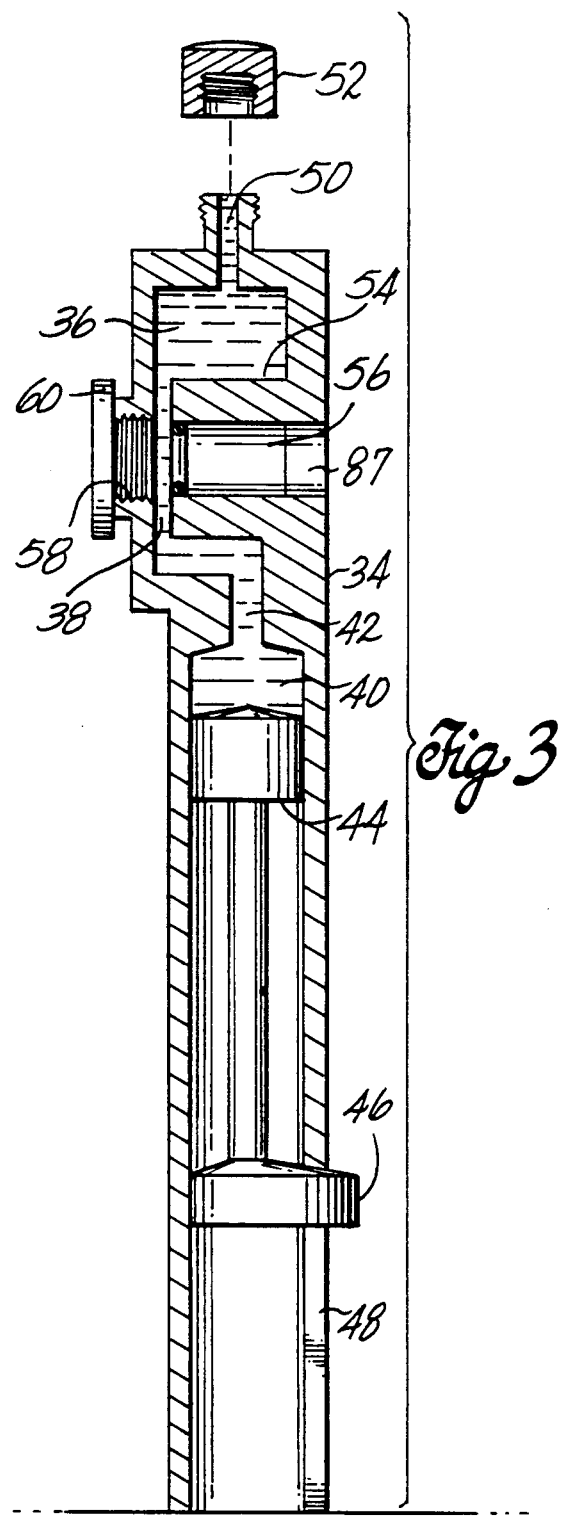
FIG. 3 is a side sectional view of a glucose monitoring instrument incorporating principles of the invention during preparation for taking a measurement.

3. The instrument is placed on end as shown in FIG. 3. Cap 52 is removed to permit the chamber to vent and piston 44 is retracted to withdraw buffer fluid from reservoir 36 and section 38, including the surface of membrane 80. Any residual moisture can be removed from the surface of membrane 80 by a dry absorbent nonreactive piece of cloth or toweling. Cap 52 is replaced.

Figure 4:
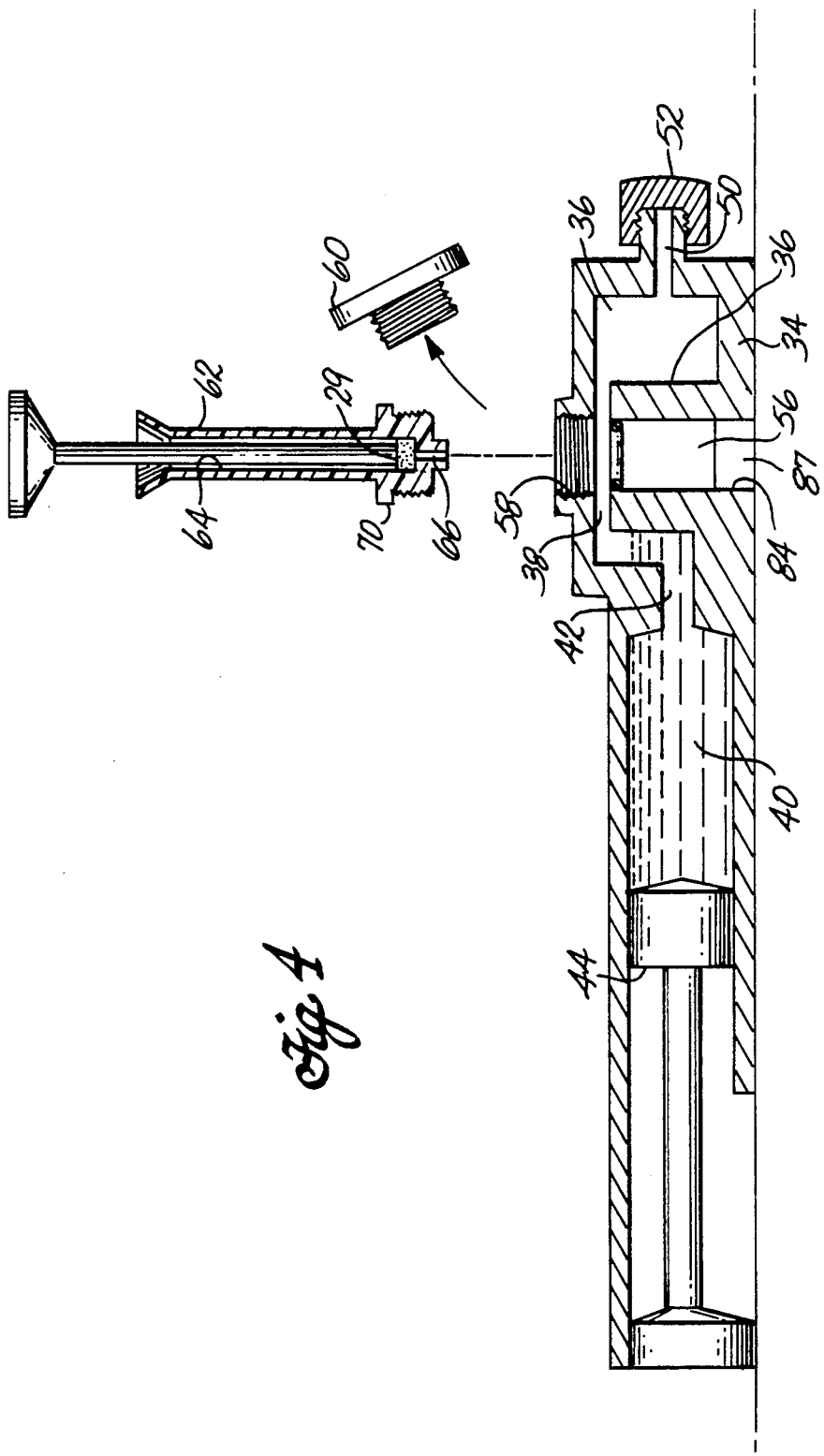
FIG. 4 is a side sectional view of the instrument of FIG. 3 immediately prior to introduction of a fluid specimen.
Figure 5:
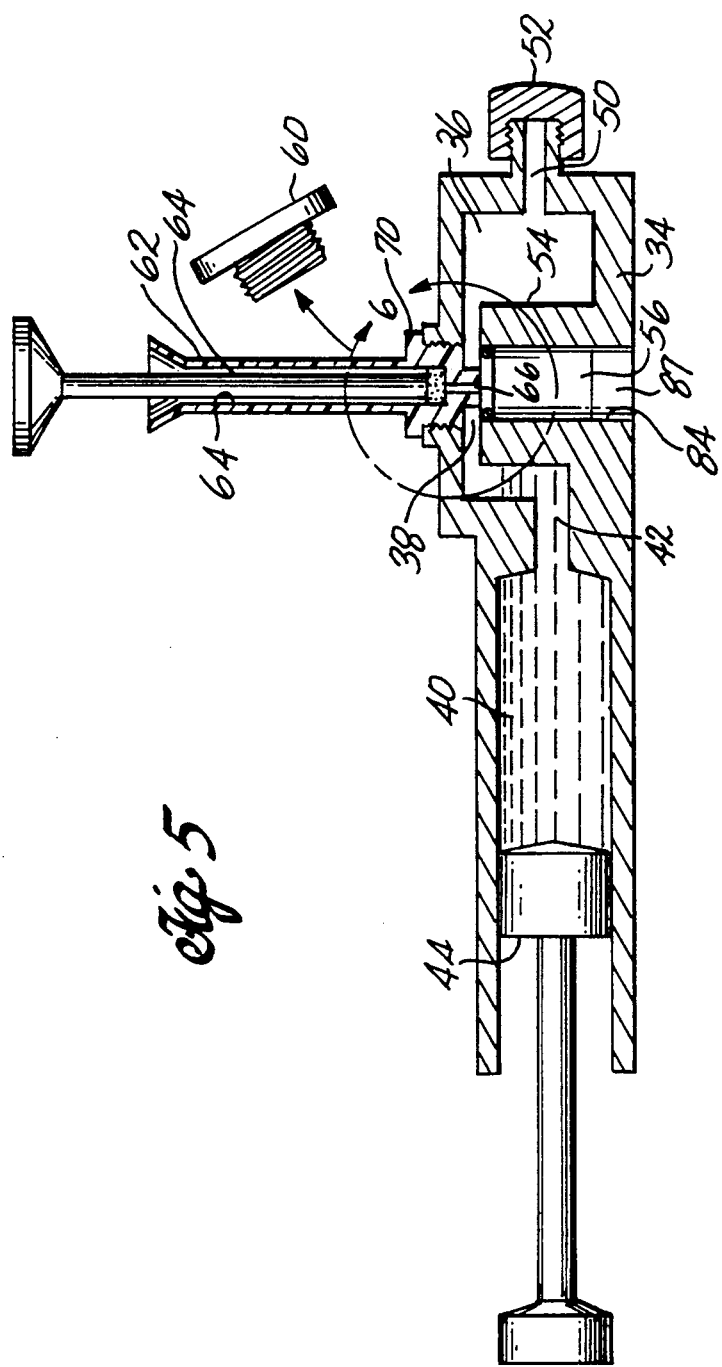
FIG. 5 is a side sectional view of the instrument of FIG. 3 during the measurement of a fluid sample.
Figure 6:
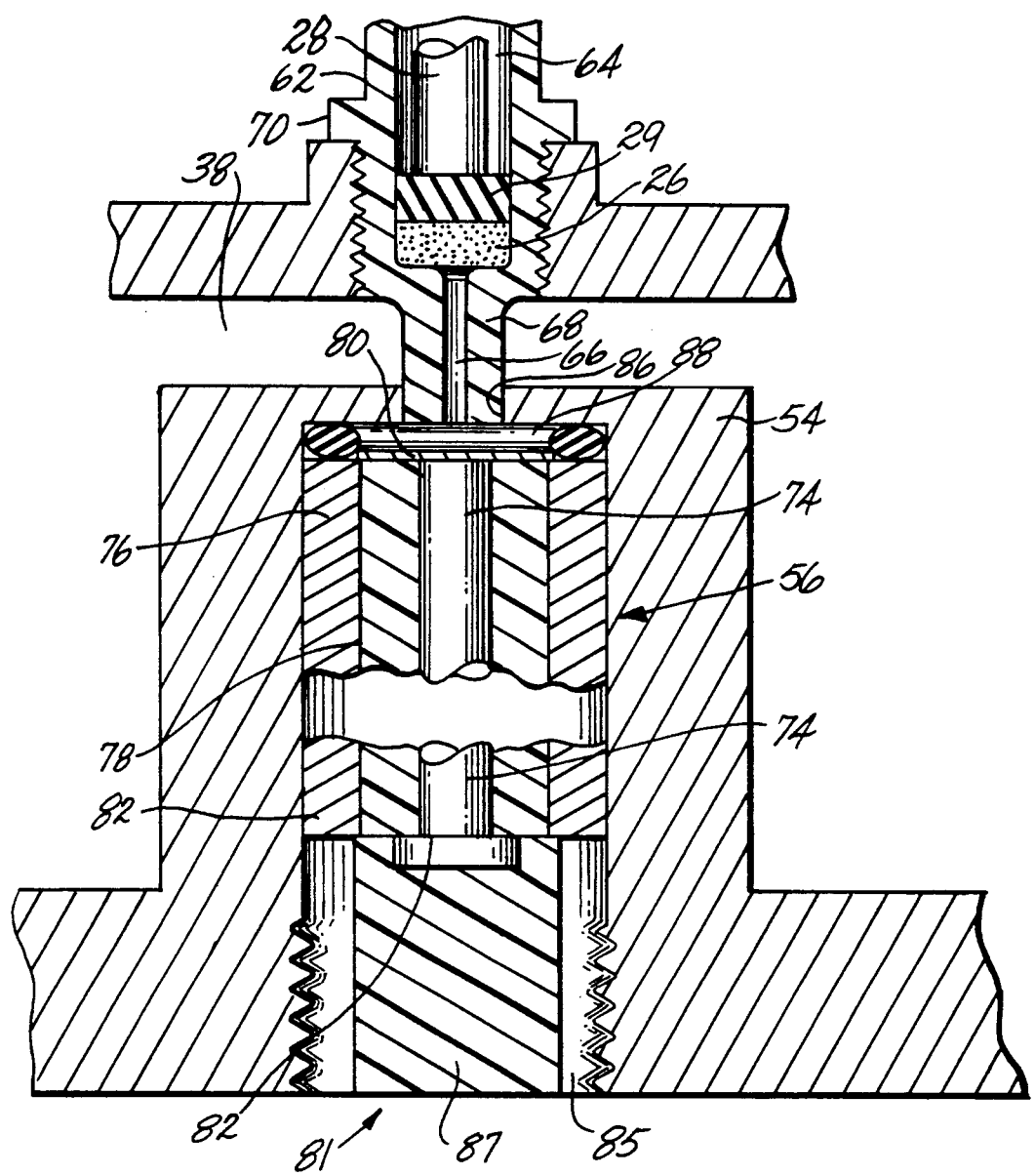
FIG. 6 is an enlargement of part of FIG. 5 illustrating the enzyme electrode and collector system in greater detail.

4. The instrument is rotated from the upright position, as shown in FIG. 3, to a flat position, as shown in FIG. 4. Cap 60 is removed in preparation for delivery of a sample to the instrument.

5. Concentrator 27 is screwed into port 58 until flange 70 abuts the outer surface of housing 34.

6. Wand 25 is inserted into bore 64 of concentrator 62, collecting swab 26 first and piston 29 is pushed to the end thereof to squeeze the fluid sample from collecting swab 26. Because of the small diameter of exit opening 66 a great deal of pressure is built up to assist the extraction of the sample from collecting swab 26.

7. The sample fluid forced out of collecting swab 26 flows through exit opening 66 into well 88. By virtue of the small cell size of collecting swab 26, the viscous glycoprotein of the sample is retained by the collecting swab as the aqueous low viscosity glucose solution is expelled. As a result, few air bubbles are formed in the fluid sample delivered to the membrane and good fluid-membrane contact is achieved in the monitoring instrument. It has been found that sufficient oxygen is present to insure that the hydrogen peroxide produced by the chemical reaction is directly related to the glucose level in the sample. To control the uniformity of the volume of the sample subjected to measurement, the fluid absorbing capacity of collecting swab 26 is larger than the volume of well 88. Thus, well 88 is always completely filled with sample fluid. The pressure created by piston 29 urges the sample fluid to move through membrane 80. As the fluid sample passes through membrane 80, the chemical reaction described in U.S. Pat. No. 3,979,274 occurs to produce between anode 74 and cathode 76 a small electrical current. (query: where does the oxygen come from?) The electric current is sensed as described below to produce a glucose level reading. Concentrator 62 is unscrewed from port 58 and cap 60 is replaced.

8. The instrument is again placed on end as shown in FIG. 3. Cap 52 is removed to vent reservoir 36 and piston 44 is depressed to return buffer fluid to reservoir 36, section 38, and the surface of membrane 80. Cap 52 is replaced to complete the procedure.

Figure 7:
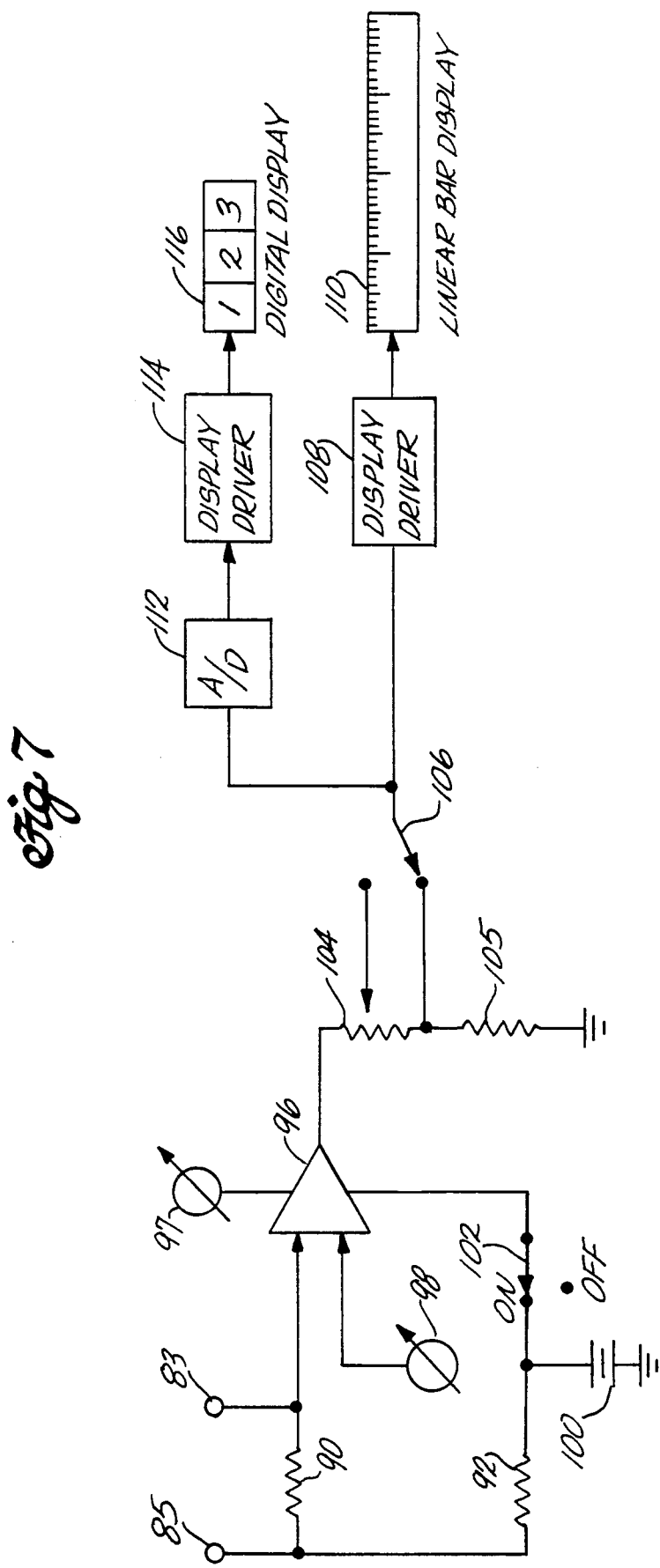
FIG. 7 is a schematic diagram of the electronic circuitry for generating an electrical readout and visual display of measured glucose level values.

In FIG. 7 is shown the electronic circuitry incorporated in the instrument to sense the electric current produced by the chemical reaction. Contact 83 is connected to one input of a differential amplifier 96. An adjustable current controlled by a zero set knob 98 is applied to the other input of differential amplifier 96. DC power from a source 100 is applied through an ON-OFF switch 102 to amplifier 96. Contact 85 is connected by a resistor 90 to contact 83 and by a resistor 92 to the ungrounded terminal of source 100. Resistors 90 and 92 serve as a voltage divider to impress a small e.g., 700 millivolts) permanent polarizing potential between cathode 74 and anode 76. The gain of amplifier 96 can be adjusted by a calibration knob 97. Voltage dividing resistors 104 and 105 are connected from the output of amplifier 96 to ground. A mode switch 106 has a wiper arm that can be moved between a high resistance to ground terminal for oral fluid measurement and a low resistance to ground terminal for blood whole blood measurement. The high resistance to ground terminal is adjustable. Switch 106 is coupled to a display driver 108 which actuates a linear bar display 110. The current produced by the chemical reaction is time dependent. Therefore, each reading is made by the described circuitry the same time after the sample is delivered to electrode 56, e.g., after 30 seconds.

Alternatively, switch 106 could be coupled by an analog-to-digital (A/D) convertor 112 to a digital display driver 114. a digital display 116 is actuated by driver 114.

Display driver 108 is shown in more detail in FIG. 8. Switch 106 is coupled to a first input of a comparator 118. Lamps 120a, 120b, ... 120n are physically arranged adjacent to each other in a straight line to form a linear bar display. Electrically, lamps 120a, 120b, ... 120n are connected in series with internal or external resistances 122a, 122b, ... 122n, respectively, and a resistor 124 across a DC voltage source 126. The junction of resistor 124 and the chain of lamps is connected to a second input of comparator 118. Comparator 118 has a binary output, the value of which depends upon which input has a higher voltage value. The resistor-lamp pairs are shunted by switches 128a, 128b, ... 128n, respectively. The output of comparator 118 and the output of a source of clock pulses 130 are connected to the inputs of an AND gate 132. The output of AND gate 132 is connected to the count input of a counter 134. Depending upon the state of counter 134, a decoder 136 actuates selected combinations of switches 128a, 128b, ... 128n to short circuit corresponding resistor-lamp combinations, thereby varying the voltage applied to the second input of comparator 118, and turning off some of lamps 120a, 120b, ... 120n.

In operation, each time a new value of voltage is applied to the first input of comparator 118 by switch 106, counter 134 is reset. Thereupon, decoder 136 controls switches 128a, 128b, ... 128n to open switches 128a, 128b, ... 128n in sequence from the bottom up responsive to the clock pulses from source 130 until the voltage at the second input of comparator 118 rises to the value at the first input thereof. At such time, the binary value at the output of comparator 118 changes and AND gate 132 stops transmitting clock pulses to counter 134. As switches 128a, 128b, ... 128n open in sequence, lamps 120a, 120b, ... 120n light up, thereby increasing the length of the visible bar sequentially until the two inputs to comparator 118 are equal. To display a new reading, counter 134 is reset and the process is repeated.

FIGS. 9 and 10 illustrate an outer case 138 of the glucose monitoring instrument. A tablet of sheets of paper 140 is mounted on a front face 142 of outer case 138. Each sheet of tablet 140 has imprinted thereon a graph 144 in rectangular coordinates. The ordinate of the graph has glucose level graduations corresponding to the graduations on display 110. The abscissa of graph 144 has graduations representing the time of day in two-hour increments. Tablet 140 is secured to front face 142 adjacent to linear bar display 110 by a clamp 143 with graph 144 so positioned that the graduations of the ordinate are aligned with the graduations of the increments of display 110. To record a reading that appears on display 110, the user simply moves laterally to the appropriate time of day and marks the sheet of paper. For example, at 8:00 A.M. a reading of 120 mg/dl is recorded. And at 2:00 P.M. a reading of 230 mg/dl is recorded. At the end of the day the user simply tears off and saves the current sheet in preparation for logging glucose readings for the next day.

The described embodiments of the invention are only considered to be preferred and illustrative of the inventive concept; the scope of the invention is not to be restricted to such embodiments. Various and numerous other arrangements may be devised by one skilled in the art without departing from the spirit and scope of this invention.

What is claimed is:

1. A method for monitoring glucose comprising the steps of:

placing a nonreactive absorbent collecting swab in contact with a surface of the oral cavity of a patient to collect thereon a sample of glucose level indicative oral fluid;

removing the collecting swab from the oral cavity;

transferring the sample from the collecting swab to an enzyme electrode off site of the patient;

sensing an electric current produced by the enzyme electrode in response to the sample and displaying the sensed electric current to indicate glucose level.

2. The method of claim 1, in which the collecting swab is placed in contact with a surface of the oral cavity at the junction of the superior labial mucous membrane and the superior gingivae between the upper canine teeth.

3. The method of claim 1, in which the collecting swab is an open cell foam material with a cell size in the order of 0.3 mm in diameter.

4. The method of claim 3, in which the collecting swab is secured to a piston that rides in a cylinder open at one end and having a small hole at the other end, the transferring step comprising pushing the piston against the other end of the cylinder to squeeze the sample through the small hole.

5. A method for monitoring glucose comprising the steps of:

applying to an enzyme electrode a sample of glucose level indicative oral fluid taken from a surface of the oral cavity of a patient at the junction of the superior labial mucous membrane and the superior gingivae between the upper canine teeth;

sensing the electric current produced by the enzyme electrode in response to the sample; and displaying the sensed electric current to indicate glucose level.

* * * * *